United States Patent
Aiello

(10) Patent No.: US 9,117,638 B2
(45) Date of Patent: Aug. 25, 2015

(54) INTELLIGENT BACKGROUND DATA ACQUISITION AND SUBTRACTION

(71) Applicant: DH TECHNOLOGIES DEVELOPMENT PTE. LTD., Singapore (SG)

(72) Inventor: Mauro Aiello, Brampton (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/365,982

(22) PCT Filed: Nov. 28, 2012

(86) PCT No.: PCT/IB2012/002528
§ 371 (c)(1),
(2) Date: Jun. 16, 2014

(87) PCT Pub. No.: WO2013/098601
PCT Pub. Date: Jul. 4, 2013

(65) Prior Publication Data
US 2014/0319336 A1    Oct. 30, 2014

Related U.S. Application Data

(60) Provisional application No. 61/581,676, filed on Dec. 30, 2011.

(51) Int. Cl.
| | | |
|---|---|---|
| *B01D 59/44* | (2006.01) | |
| *H01J 49/00* | (2006.01) | |
| *H01J 49/28* | (2006.01) | |
| *G01N 27/62* | (2006.01) | |
| *G01N 30/72* | (2006.01) | |

(52) U.S. Cl.
CPC .......... *H01J 49/0031* (2013.01); *G01N 27/622* (2013.01); *H01J 49/004* (2013.01); *G01N 30/72* (2013.01)

(58) Field of Classification Search
USPC ............ 250/281, 282, 288, 299, 390.07, 526; 73/23.2, 23.37
See application file for complete search history.

(56) References Cited

U.S. PATENT DOCUMENTS

| | | | |
|---|---|---|---|
| 5,672,869 A | 9/1997 | Windig et al. | |
| 7,668,697 B2 * | 2/2010 | Volkov et al. | 702/187 |

(Continued)

FOREIGN PATENT DOCUMENTS

| | | |
|---|---|---|
| JP | 2000-206103 A | 7/2000 |
| JP | 2005-221276 A | 8/2005 |
| JP | 2011-058930 A | 3/2011 |

OTHER PUBLICATIONS

International Search Report for PCT/IB2012/002528, mailed Mar. 28, 2013.

*Primary Examiner* — Bernard E Souw
(74) *Attorney, Agent, or Firm* — John R. Kasha; Kelly L. Kasha; Kasha Law LLC

(57) ABSTRACT

A scan of a separating sample mixture is received from a mass spectrometer at each interval of a plurality of intervals. It is determined at a first interval that a received mass spectrometry scan at the first interval and one or more preceding received mass spectrometry scans include a varying ion signal that represents an ion of a known compound and has an intensity above a threshold level. The mass spectrometer is instructed to perform a dependent scan for the ion at the first interval producing a spectrum for the known compound. A second interval is selected after the first interval where the varying ion signal has an intensity that is not above the threshold level. The mass spectrometer is instructed to perform a dependent scan for the ion at the second interval producing a spectrum for a background.

15 Claims, 6 Drawing Sheets

(56) References Cited

U.S. PATENT DOCUMENTS

| | | | |
|---|---|---|---|
| 8,803,083 B2* | 8/2014 | Goldberg | 250/287 |
| 2009/0302213 A1* | 12/2009 | Kuehl et al. | 250/282 |
| 2010/0187414 A1 | 7/2010 | Gorenstein et al. | |
| 2010/0213368 A1* | 8/2010 | Wang et al. | 250/282 |
| 2012/0126110 A1* | 5/2012 | Green et al. | 250/282 |
| 2013/0048852 A1* | 2/2013 | Verenchikov | 250/282 |
| 2014/0138526 A1* | 5/2014 | Goldberg | 250/252.1 |

* cited by examiner

INTELLIGENT BACKGROUND DATA ACQUISITION AND SUBTRACTION

RELATED APPLICATION

This application claims priority to U.S. provisional application No. 61/581,676 filed Dec. 30, 2011, which is incorporated herein by reference in its entirety.

INTRODUCTION

Mass spectrometers are often coupled with chromatography systems in order to identify and characterize eluting species from a test sample. In such a coupled system, the eluting solvent is ionized and a series of time-varying mass spectral images are obtained of the eluting solvent at specified time intervals producing a chromatogram, or a collection of mass spectra. These time intervals range from, for example, 1 second to 100 minutes or greater. As the test sample may contain many species or compounds, it is often desirable to be able to automatically determine or identify species or compounds of interest as they elute and perform tandem mass spectrometry, or mass spectrometry/mass spectrometry (MS/MS), analysis to characterize them.

An exemplary and well-known system for identifying compounds of interest as they elute and performing tandem mass spectrometry is the information dependent acquisition (IDA) system marketed by AB Sciex. During the data acquisition process this software identifies a peak in a collection of mass spectra so as to select a precursor ion. The software then directs one or more subsequent stages of mass spectrometry, such as MS/MS or mass spectrometry/mass spectrometry/mass spectrometry (MS/MS/MS), in which the chosen precursor ion is fragmented. A compound of interest is then characterized or verified by searching a library for a match with the product ion, or fragment ion, spectrum.

Often, however, a product ion spectrum obtained from such a system and matched against a library includes isobaric co-eluting ions or background ions in addition to the ions of interest. Consequently, the library search produces results of poor quality.

SUMMARY

In accordance with various aspects of the applicant's teachings, there is provided a system for automatically triggering a dependent mass spectrometry scan for a background signal during data acquisition, comprising a separation device that separates one or more compounds from a sample mixture; a mass spectrometer that performs a mass spectrometry scan on the separating sample mixture at a plurality of intervals; and a processor that receives from the mass spectrometer each mass spectrometry scan at each interval of the plurality of intervals, determines at a first interval of the plurality of intervals that a received mass spectrometry scan at the first interval and one or more preceding received mass spectrometry scans include a varying ion signal that represents an ion of a known compound and that has an intensity above a threshold level, instructs the mass spectrometer to perform a dependent mass spectrometry scan of the separating sample mixture for the ion at the first interval producing a spectrum for the known compound, selects a second interval of the plurality of intervals that is after the first interval and where the varying ion signal has an intensity that is not above the threshold level, and instructs the mass spectrometer to perform a dependent mass spectrometry scan of the separating sample mixture for the ion at the second interval producing a spectrum for a background.

In various aspects, the processor can select the second interval by determining at each interval of the plurality of intervals after the first interval an intensity of the varying ion signal from a received mass spectrometry scan at the each interval and selecting the each interval as the second interval if the intensity is not above the threshold level. In various aspects, the processor can select the second interval by adding an amount to the first interval. In various embodiments, the processor can further calculate a corrected spectrum for the known compound from the spectrum for the known compound and the spectrum for the background.

In various aspects, the processor can further calculate a corrected spectrum for the known compound by subtracting the spectrum for the background from the spectrum for the known compound. In various aspects, the processor can further calculate a corrected spectrum for the known compound during data acquisition.

In various embodiments, the processor can further calculate a corrected spectrum for the known compound after data acquisition.

In accordance with various aspects of the applicant's teachings, there is provided a method for automatically triggering a dependent mass spectrometry scan for a background signal during data acquisition, comprising instructing a mass spectrometer to perform a scan on a separating sample mixture at a plurality of intervals, wherein a separation device separates one or more compounds from a sample mixture producing the separating sample mixture; determining at a first interval of the plurality of intervals that a mass spectrometry scan at the first interval and one or more preceding mass spectrometry scans include a varying ion signal that represents an ion of a known compound and that has an intensity above a threshold level; instructing the mass spectrometer to perform a dependent mass spectrometry scan of the separating sample mixture for the ion at the first interval producing a spectrum for the known compound; selecting a second interval of the plurality of intervals that is after the first interval and where the varying ion signal has an intensity that is not above the threshold level; and instructing the mass spectrometer to perform a dependent mass spectrometry scan of the separating sample mixture for the ion at the second interval producing a spectrum for a background. In various aspects, selecting a second interval of the plurality of intervals can comprise determining at each interval of the plurality of intervals after the first interval an intensity of the varying ion signal from a received mass spectrometry scan at the each interval and selecting the each interval as the second interval if the intensity is not above the threshold level. In various aspects, selecting a second interval of the plurality of intervals can comprise adding an amount to the first interval. In various embodiments, the method can further comprise calculating a corrected spectrum for the known compound from the spectrum for the known compound and the spectrum for the background. In various aspects, calculating a corrected spectrum for the known compound from the spectrum for the known compound and the spectrum for the background comprises subtracting the spectrum for the background from the spectrum for the known compound. In various aspects, calculating a corrected spectrum for the known compound from the spectrum for the known compound and the spectrum for the background occurs during data acquisition. In various aspects, calculating a corrected spectrum for the known compound from the spectrum for the known compound and the spectrum for the background occurs after data acquisition.

In accordance with various aspects of the applicant's teachings, there is provided a computer program product, comprising a non-transitory and tangible computer-readable storage medium whose contents include a program with instructions being executed on a processor so as to perform a method for automatically triggering a dependent mass spectrometry scan for a background signal during data acquisition, the method comprising providing a system, wherein the system comprises one or more distinct software modules, and wherein the distinct software modules comprise a measurement module, an analysis module, and a dependent scan control module; instructing a mass spectrometer to perform a scan on a separating sample mixture at a plurality of intervals using the measurement module, wherein a separation device separates one or more compounds from a sample mixture producing the separating sample mixture; determining at a first interval of the plurality of intervals that a mass spectrometry scan at the first interval and one or more preceding mass spectrometry scans include a varying ion signal that represents an ion of a known compound and that has an intensity above a threshold level using the analysis module; instructing the mass spectrometer to perform a dependent mass spectrometry scan of the separating sample mixture for the ion at the first interval producing a spectrum for the known compound using the dependent scan control module; selecting a second interval of the plurality of intervals that is after the first interval and where the varying ion signal has an intensity that is not above the threshold level using the analysis module; and instructing the mass spectrometer to perform a dependent mass spectrometry scan of the separating sample mixture for the ion at the second interval producing a spectrum for a background using the dependent scan control module.

BRIEF DESCRIPTION OF THE DRAWINGS

The skilled artisan will understand that the drawings, described below, are for illustration purposes only. The drawings are not intended to limit the scope of the present teachings in any way.

Figure 1:
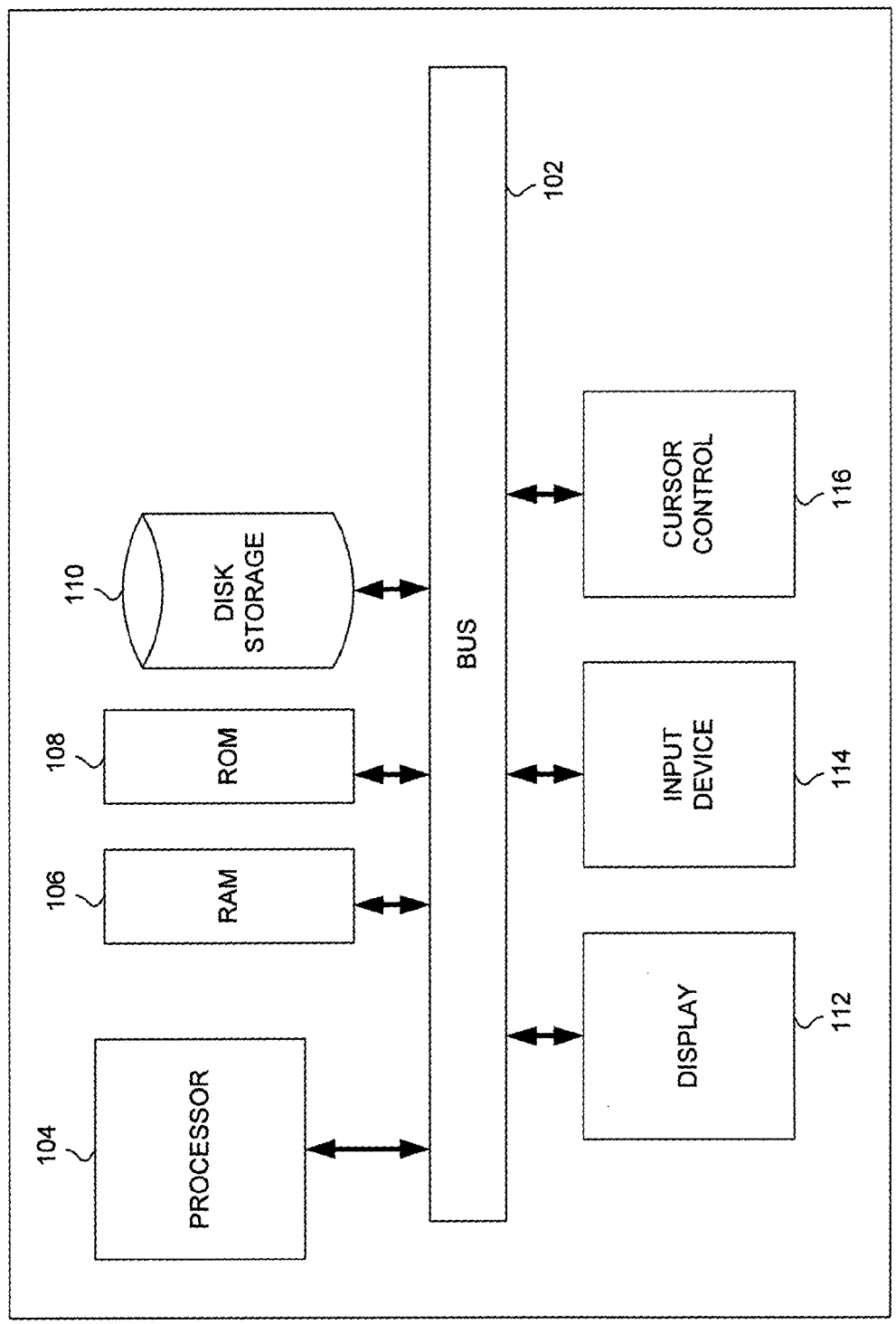
FIG. 1 is a block diagram that illustrates a computer system, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Automated Background Subtraction

As described above, mass spectrometers coupled with separation systems are used to automatically identify and characterize compounds of interest as they separate over time and perform mass spectrometry analysis to characterize them. An exemplary automated mass spectrometry acquisition system for identifying compounds of interest as they separate and characterizing their composition using mass spectrometry analysis is the information dependent acquisition (IDA). Mass spectrometry analysis is performed using a dependent scan, for example.

Often, however, such systems produce poor library search results due to co-eluting ions or background ions included in the dependent scan. A dependent scan can include, but is not limited to, a mass spectrometry/mass spectrometry (MS/MS) scan, a fragment ion scan, a product ion scan, an enhanced product ion scan, or a mass spectrometry/mass spectrometry/mass spectrometry (MS/MS/MS) scan.

In various embodiments, an automated mass spectrometry acquisition system automatically triggers a dependent scan of the background signal after each dependent scan of the compound of interest in order to allow for background correction. The dependent scan of the background signal is performed at a time later than the dependent scan of the compound of interest. The dependent scan of the background signal cannot be performed at the time of the dependent scan of the compound of interest, because the dependent scan of the background signal would then include components of the compound of interest.

In various embodiments, a dependent scan of the background signal is performed at a time after the peak of each compound of interest in the chromatogram, or collection of mass spectra, decreases to a value below a threshold level. This time can be found by monitoring the intensity of the mass peak of the compound of interest in the collection of mass spectra after the peak is detected, for example. Alternatively, the time can also include a predetermined or selected time delay value, or delta, based on the known compound of interest or the experiment, for example.

The background spectrum produced from the dependent scan of the background signal is then used to spectrally correct the compound of interest spectrum produced from the dependent scan of the compound of interest. The compound of interest spectrum is corrected by subtracting the background spectrum from the compound of interest spectrum, for example.

Figure 2:
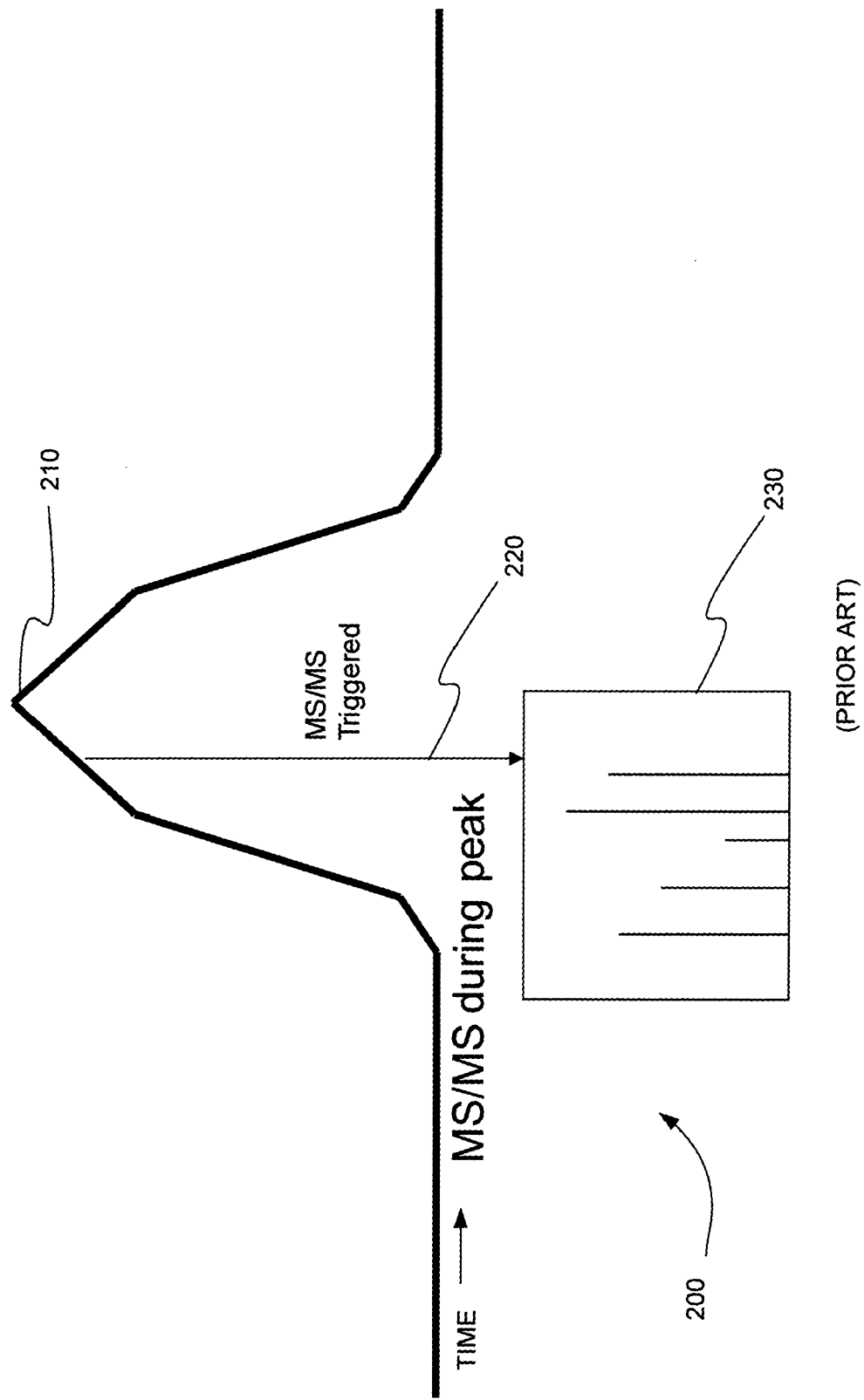
FIG. 2 is an exemplary plot of a peak from a collection of mass spectra for a compound of interest showing where in time a dependent scan is triggered by a traditional automated mass spectrometry acquisition system.

FIG. 2 is an exemplary 200 plot of a peak 210 from a collection of mass spectra for a compound of interest showing where in time a dependent scan is triggered by a traditional automated mass spectrometry acquisition system. In plot 200 a dependent scan is triggered at time 220. Dependent scan is triggered as peak 210 is rising, for example. The dependent scan produces spectrum 230. Dependent scan is an MS/MS scan and spectrum 230 is a product ion spectrum, for example. No background spectra are available to for use in correcting spectrum 230 at time 220.

Figure 3:
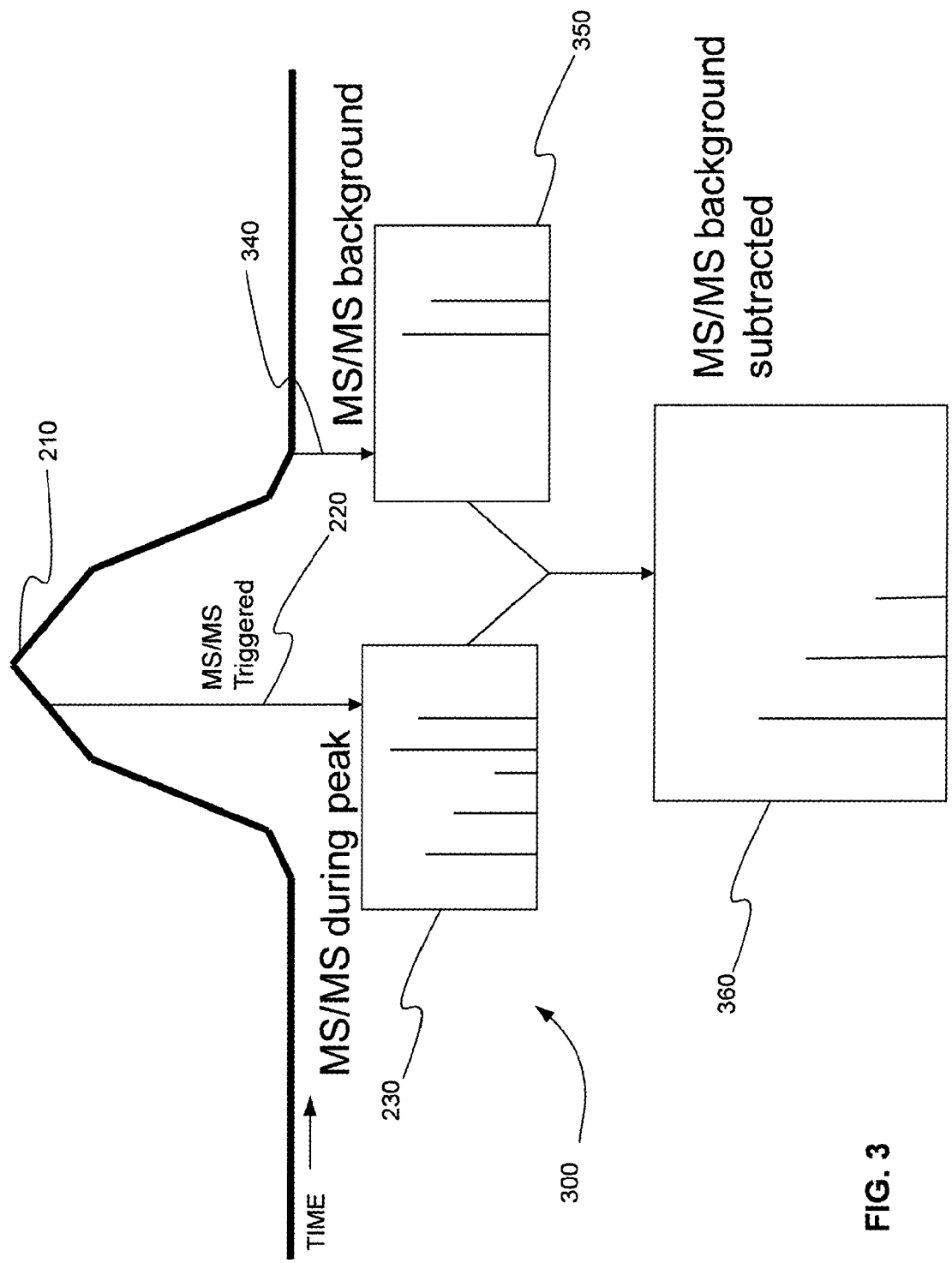
FIG. 3 is an exemplary plot of a peak from a collection of mass spectra for a compound of interest showing where in time a dependent scan of the background is triggered by an automated mass spectrometry acquisition system, in accordance with various embodiments.

FIG. 3 is an exemplary 300 plot of a peak 210 from a collection of mass spectra for a compound of interest showing where in time a dependent scan of the background is triggered by an automated mass spectrometry acquisition system, in accordance with various embodiments. In plot 300, a dependent scan of the compound of interest is triggered at time 220. This dependent scan produces compound of interest spectrum 230.

A dependent scan of the background is triggered at time 340. Time 340 is a time after time 220. Time 340 is a time at which peak 210 has decreased to a threshold level, for example. Alternatively, time 340 is determined from a predetermined or selected time delay that is added to time 200 to get time 340, for example.

The dependent scan performed at time 340 produces background spectrum 350. The dependent scan performed at time 340 is the same type of mass spectrometry scan that is performed at time 220. For example, if the dependent scan preformed at time 220 is an MS/MS scan, then an MS/MS scan is also performed at time 340.

Spectrum 360 is a spectrum that is calculated from spectrum 230 and spectrum 350. Spectrum 360 is a spectrum of the compound of interest with the background removed. Spectrum 360 is produced by subtracting spectrum 350 from spectrum 230, for example.

In various embodiments, for each peak of interest found in a collection of mass spectra a dependent scan of the background is triggered at a time after the dependent scan for the peak of interest is performed. The resulting spectrum of the dependent scan of the background is then used to correct the spectrum of the dependent scan for the peak of interest. The spectra of the plurality of dependent scans for peaks of interest are corrected after data acquisition, for example. In various embodiments and alternatively, the spectra of the plurality of dependent scans for peaks of interest can be corrected in real-time during data acquisition. For example, each spectrum of each peak of interest can be corrected immediately after the acquisition of the corresponding spectrum the background. The correction of spectra of compounds of interest is done in real-time if further data acquisition is dependent on the results of that correction.

Systems and Methods of Data Processing

Separation Coupled Mass Spectrometry System

Figure 4:
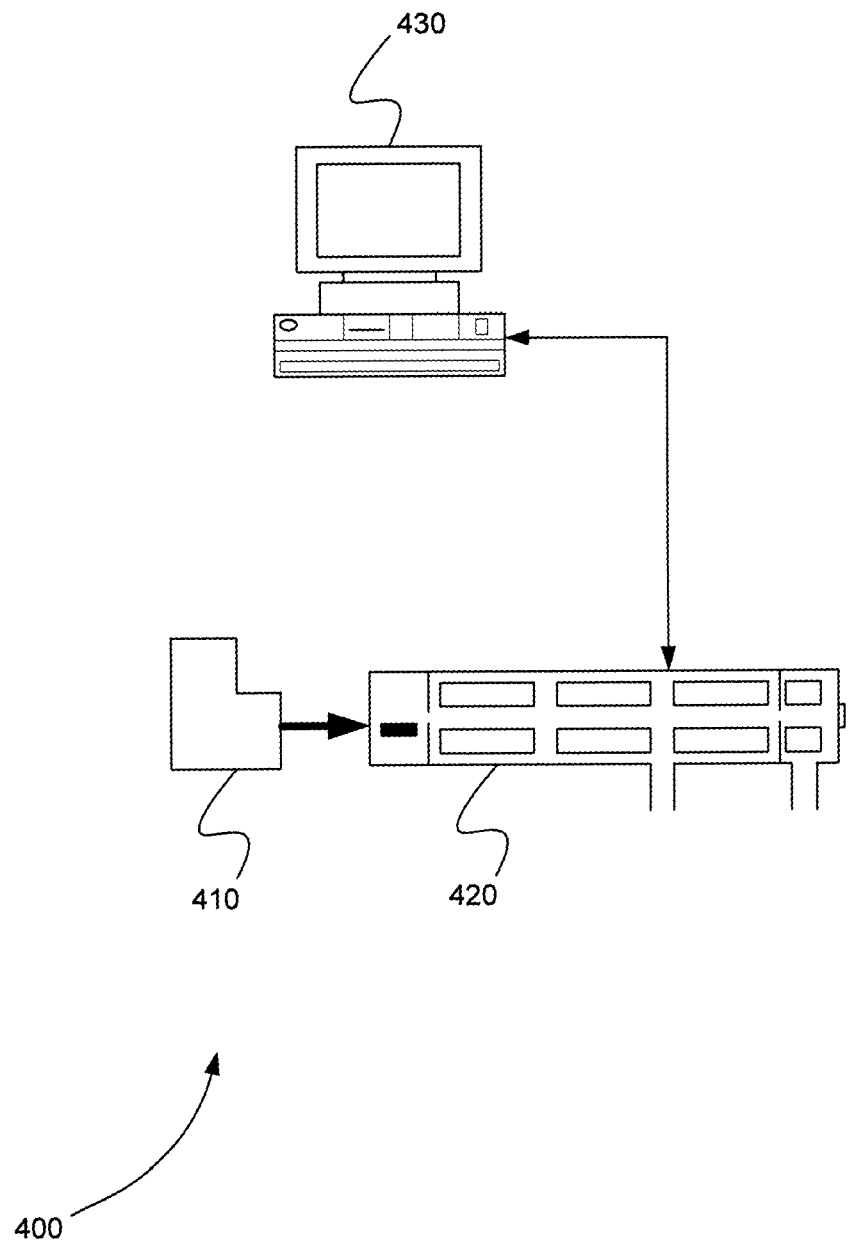
FIG. 4 is a schematic diagram showing a system for automatically triggering a dependent mass spectrometry scan for a background signal during data acquisition, in accordance with various embodiments.

FIG. 4 is a schematic diagram showing a system 400 for automatically triggering a dependent mass spectrometry scan for a background signal during data acquisition, in accordance with various embodiments. System 400 includes separation device 410, mass spectrometer 420, and processor 430. Separation device 410 separates one or more compounds from a sample mixture. Separation device 410 can include, but is not limited to, an electrophoretic device, a chromatographic device, or a mobility device.

Mass spectrometer 420 performs a mass spectrometry scan, or survey scan, on the separating sample mixture from separation device 410 at a plurality of intervals. The plurality of intervals can be, but are not limited to, a plurality of time intervals or a plurality of ion mobilities. Mass spectrometer 420 is a tandem mass spectrometer, for example. A tandem mass spectrometer can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, a magnetic four-sector mass analyzer, a hybrid quadrupole time-of-flight (Q-TOF) mass analyzer, or a Fourier transform mass analyzer. Mass spectrometer 420 can include separate mass spectrometry stages or steps in space or time, respectively.

Processor 430 is in communication with tandem mass spectrometer 420. Processor 430 can also be in communication with separation device 410. Processor 430 can be, but is not limited to, a computer, microprocessor, or any device capable of sending and receiving control signals and data to and from tandem mass spectrometer 420 and processing data.

Processor 430 receives from tandem mass spectrometer 420 each mass spectrometry scan at each time interval of the plurality of intervals. As a result, a collection of mass spectra can be created piecewise in real-time as the sample mixture is separating. The collection of mass spectra can include, but is not limited to, a chromatogram, a mass spectrogram, or mass spectra for a series of ion mobilities.

Processor 430 determines at a first time interval of the plurality of intervals that a received mass spectrometry scan at the first interval and one or more preceding received mass spectrometry scans include a varying ion signal that represent an ion of a known compound. In other words, a varying ion signal is determined from the current scan and one or more previous scans at each interval. The varying ion signal can vary over time intervals or ion mobilities, for example. The varying ion signal is a peak in the collection of mass spectra, for example.

Processor 430 instructs mass spectrometer 420 to perform a dependent mass spectrometry scan of the separating sample mixture for the ion at the first interval producing a spectrum for the known compound. Processor 430 selects a second interval of the plurality of intervals that is after the first interval. Processor 430 also selects the second interval where the varying ion signal has an intensity that is not above the threshold level. The second interval is therefore selected where only the background signal or signals for other separating analytes exist.

Processor 430 instructs mass spectrometer 420 to perform a dependent mass spectrometry scan of the separating sample mixture for the ion at the second interval producing a spectrum for a background. The background can include, but is not limited to, background signals, noise signals, or signals from other separating analytes. The background signal can include isobaric co-eluting ions or background ions, for example.

In various embodiments, processor 430 selects the second interval by determining at each subsequent interval after the first interval an intensity of the varying ion signal. The intensity is determined from the received mass spectrometry scan received at each subsequent interval. A subsequent interval is selected as the second interval, if the intensity at the subsequent interval is not above the threshold level. In other words, a subsequent interval is selected as the second interval if there is no detectable peak in the collection of mass spectra at the subsequent interval.

In various embodiments, processor 430 selects the second interval by adding an amount to the first interval. The predetermined amount can be, but is not limited to, a time difference or a difference in ion mobility. In other words, processor 430 selects the second interval based on an amount that was received as an input parameter or that is based on a particular experiment.

In various embodiments, processor 430 further calculates a corrected spectrum for the known compound from the spectrum for the known compound and the spectrum for the background. Processor 430 further calculates a corrected spectrum for the known compound by subtracting the spectrum for the background from the spectrum for the known compound, for example.

Processor 430 calculates a corrected spectrum for the known compound after data acquisition, for example. In other words, the spectrum for a known compound and a corresponding background are stored for each interval that a spectrum for the known compound is obtained. After acquisition each spectrum for each interval is corrected.

Alternatively, processor 430 calculates a corrected spectrum for the known compound during data acquisition. As the sample mixture is separating, each acquired spectrum for the known compound is correct using a corresponding background spectrum. A spectrum for the known compound is corrected during data acquisition if subsequent dependent scans are dependent on the corrected information, for example.

Mass Spectrometry Method

Figure 5:
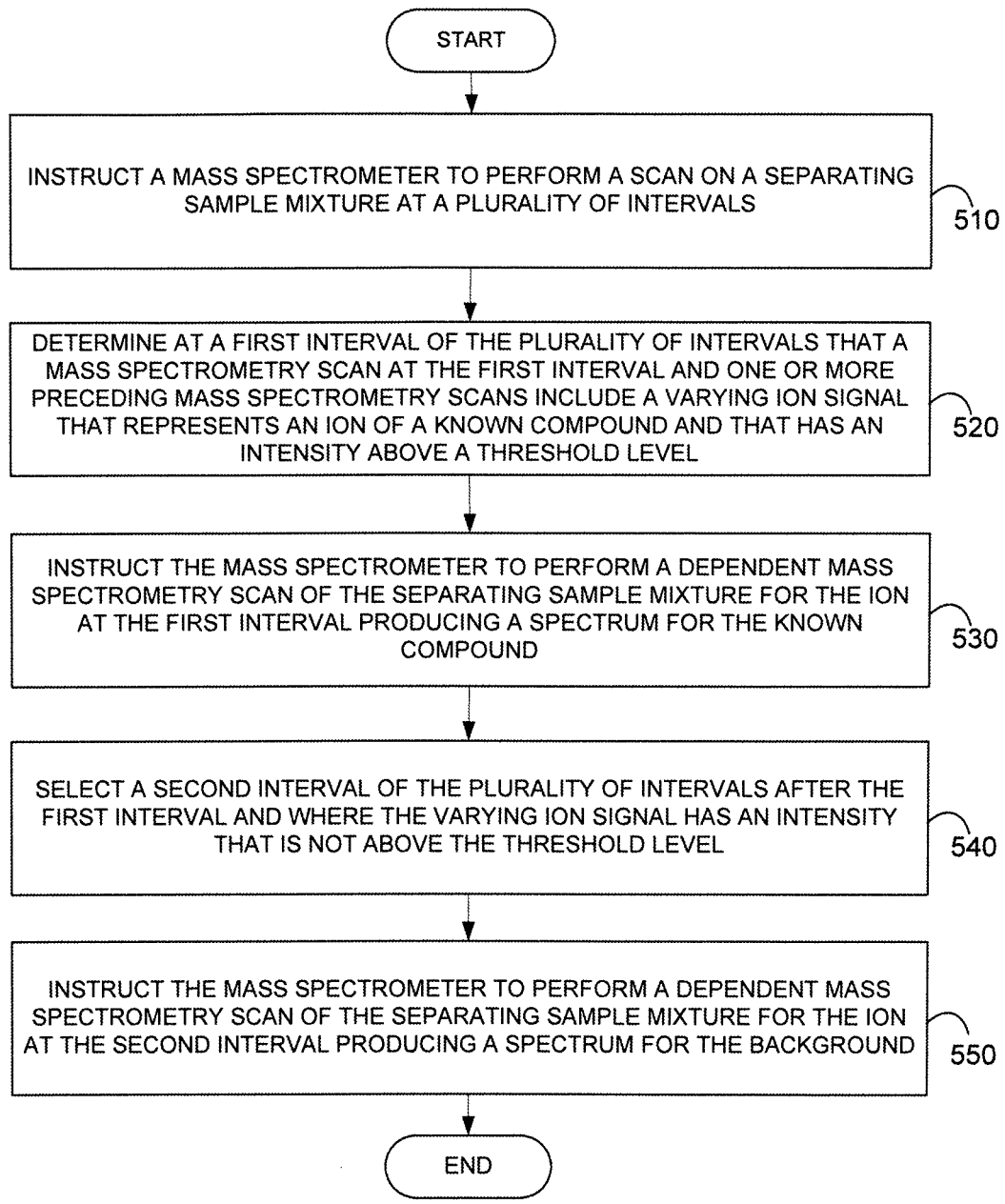
FIG. 5 is an exemplary flowchart showing a method for automatically triggering a dependent mass spectrometry scan for a background signal during data acquisition, in accordance with various embodiments.

FIG. 5 is an exemplary flowchart showing a method 500 for automatically triggering a dependent mass spectrometry scan for a background signal during data acquisition, in accordance with various embodiments.

In step 510 of method 500, a mass spectrometer is instructed to perform a scan on a separating sample mixture at a plurality of intervals. A separation device separates one or more compounds from a sample mixture producing the separating sample mixture.

In step 520, at a first interval of the plurality of intervals it is determined that a mass spectrometry scan at the first interval and one or more preceding mass spectrometry scans include a varying ion signal that represents an ion of a known compound and that has an intensity above a threshold level.

In step 530, the mass spectrometer is instructed to perform a dependent mass spectrometry scan of the separating sample mixture for the ion at the first interval producing a spectrum for the known compound.

In step 540, a second interval of the plurality of intervals is selected after the first interval and where the varying ion signal has an intensity that is not above the threshold level.

In step 550, the mass spectrometer is instructed to perform a dependent mass spectrometry scan of the separating sample mixture for the ion at the second interval producing a spectrum for the background.

Mass Spectrometry Computer Program Product

In various embodiments, a computer program product includes a non-transitory and tangible computer-readable storage medium whose contents include a program with instructions being executed on a processor so as to perform a method for automatically triggering a dependent mass spectrometry scan for a background signal during data acquisition. This method is performed by a system that includes one or more distinct software modules.

Figure 6:
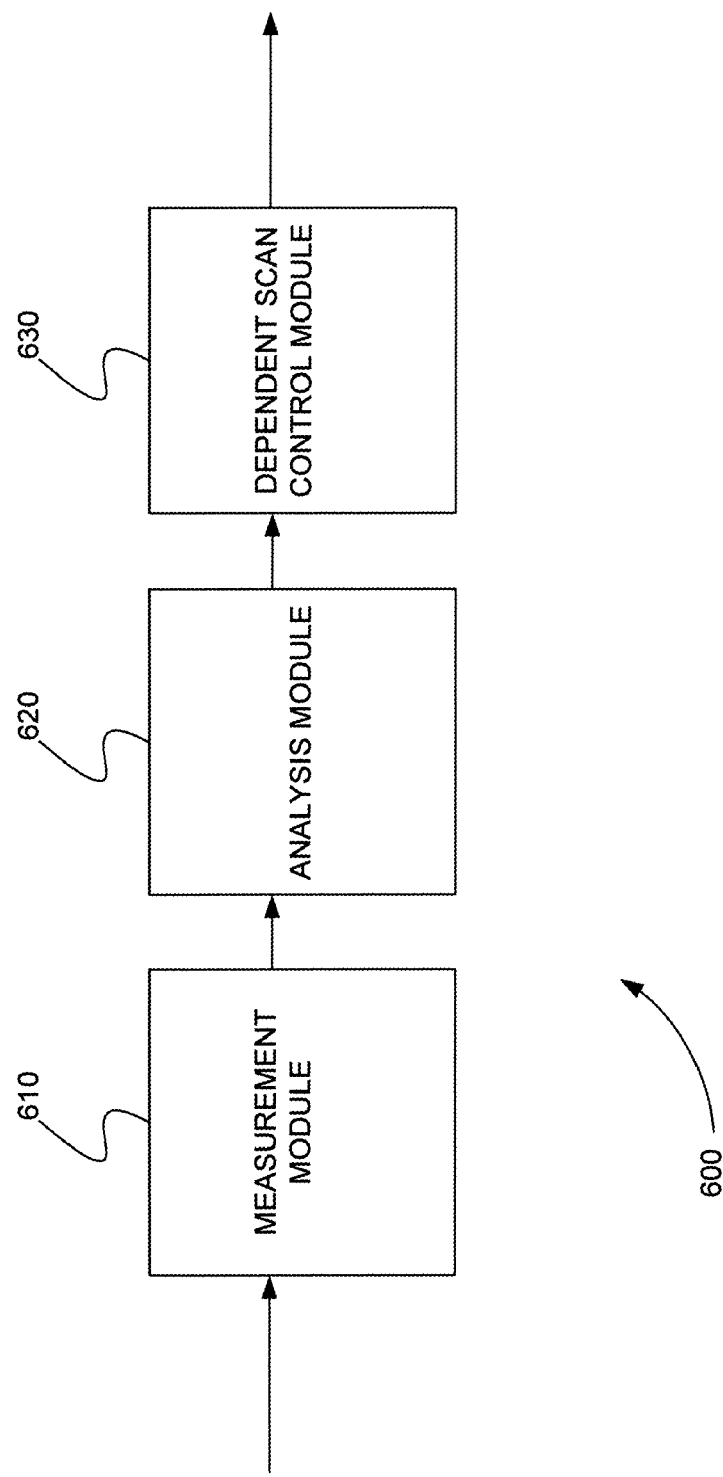
FIG. 6 is a schematic diagram of a system that includes one or more distinct software modules that perform a method for automatically triggering a dependent mass spectrometry scan for a background signal during data acquisition, in accordance with various embodiments.

FIG. 6 is a schematic diagram of a system 600 that includes one or more distinct software modules that perform a method for automatically triggering a dependent mass spectrometry scan for a background signal during data acquisition, in accordance with various embodiments. System 600 includes measurement module 610, analysis module 620, and dependent scan control module 630.

Measurement module 610 instructs a mass spectrometer to perform a scan on a separating sample mixture at a plurality of intervals. A separation device separates one or more compounds from a sample mixture producing the separating sample mixture.

Analysis module 620 determines at a first interval of the plurality of intervals that a mass spectrometry scan at the first interval and one or more preceding mass spectrometry scans include a varying ion signal that represents an ion of a known compound and that has an intensity above a threshold level.

Dependent scan control module 630 instructs the mass spectrometer to perform a dependent mass spectrometry scan of the separating sample mixture for the ion at the first interval producing a spectrum for the known compound.

Analysis module 620 selects a second interval of the plurality of intervals that is after the first interval and where the varying ion signal has an intensity that is not above the threshold level. Finally, dependent scan control module 630 instructs the mass spectrometer to perform a dependent mass spectrometry scan of the separating sample mixture for the ion at the second interval producing a spectrum for the background.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The invention claimed is:

1. A system for automatically triggering a dependent mass spectrometry scan for a background signal during data acquisition, comprising:

a separation device that separates one or more compounds from a sample mixture;

a mass spectrometer that performs a mass spectrometry scan on the separating sample mixture at a plurality of intervals; and a processor that receives from the mass spectrometer each mass spectrometry scan at each interval of the plurality of intervals, determines at a first interval of the plurality of intervals that a received mass spectrometry scan at the first interval and one or more preceding received mass spectrometry scans include a varying ion signal that represents an ion of a known compound and that has an intensity above a threshold level, instructs the mass spectrometer to perform a dependent mass spectrometry scan of the separating sample mixture for the ion at the first interval producing a spectrum for the known compound, selects a second interval of the plurality of intervals that is after the first interval and where the varying ion signal has an intensity that is not above the threshold level, and instructs the mass spectrometer to perform a dependent mass spectrometry scan of the separating sample mixture for the ion at the second interval producing a spectrum for a background.

2. The system of claim 1, wherein the processor selects the second interval by determining at each interval of the plurality of intervals after the first interval an intensity of the varying ion signal from a received mass spectrometry scan at the each interval and selecting the each interval as the second interval if the intensity is not above the threshold level.

3. The system of claim 1, wherein the processor selects the second interval by adding an amount to the first interval.

4. The system of claim 1, wherein the processor further calculates a corrected spectrum for the known compound from the spectrum for the known compound and the spectrum for the background.

5. The system of claim 4, wherein the processor further calculates a corrected spectrum for the known compound by subtracting the spectrum for the background from the spectrum for the known compound.

6. The system of claim 4, wherein the processor further calculates a corrected spectrum for the known compound during data acquisition.

7. The system of claim 4, wherein the processor further calculates a corrected spectrum for the known compound after data acquisition.

8. A method for automatically triggering a dependent mass spectrometry scan for a background signal during data acquisition, comprising:

instructing a mass spectrometer to perform a scan on a separating sample mixture at a plurality of intervals, wherein a separation device separates one or more compounds from a sample mixture producing the separating sample mixture;

determining at a first interval of the plurality of intervals that a mass spectrometry scan at the first interval and one or more preceding mass spectrometry scans include a varying ion signal that represents an ion of a known compound and that has an intensity above a threshold level;

instructing the mass spectrometer to perform a dependent mass spectrometry scan of the separating sample mixture for the ion at the first interval producing a spectrum for the known compound;

selecting a second interval of the plurality of intervals that is after the first interval and where the varying ion signal has an intensity that is not above the threshold level; and instructing the mass spectrometer to perform a dependent mass spectrometry scan of the separating sample mixture for the ion at the second interval producing a spectrum for a background.

9. The method of claim 8, wherein selecting a second interval of the plurality of intervals comprises determining at each interval of the plurality of intervals after the first interval an intensity of the varying ion signal from a received mass spectrometry scan at the each interval and selecting the each interval as the second interval if the intensity is not above the threshold level.

10. The method of claim 8, wherein selecting a second interval of the plurality of intervals comprises adding an amount to the first interval.

11. The method of claim 8, further comprising calculating a corrected spectrum for the known compound from the spectrum for the known compound and the spectrum for the background.

12. The method of claim 11, wherein calculating a corrected spectrum for the known compound from the spectrum for the known compound and the spectrum for the background comprises subtracting the spectrum for the background from the spectrum for the known compound.

13. The method of claim 11, wherein calculating a corrected spectrum for the known compound from the spectrum for the known compound and the spectrum for the background occurs during data acquisition.

14. The method of claim 11, wherein calculating a corrected spectrum for the known compound from the spectrum for the known compound and the spectrum for the background occurs after data acquisition.

15. A computer program product, comprising a non-transitory and tangible computer-readable storage medium whose contents include a program with instructions being executed on a processor so as to perform a method for automatically triggering a dependent mass spectrometry scan for a background signal during data acquisition, the method comprising:

providing a system, wherein the system comprises one or more distinct software modules, and wherein the distinct software modules comprise a measurement module, an analysis module, and a dependent scan control module;

instructing a mass spectrometer to perform a scan on a separating sample mixture at a plurality of intervals using the measurement module, wherein a separation device separates one or more compounds from a sample mixture producing the separating sample mixture;

determining at a first interval of the plurality of intervals that a mass spectrometry scan at the first interval and one or more preceding mass spectrometry scans include a varying ion signal that represents an ion of a known compound and that has an intensity above a threshold level using the analysis module;

instructing the mass spectrometer to perform a dependent mass spectrometry scan of the separating sample mixture for the ion at the first interval producing a spectrum for the known compound using the dependent scan control module;

selecting a second interval of the plurality of intervals that is after the first interval and where the varying ion signal has an intensity that is not above the threshold level using the analysis module; and instructing the mass spectrometer to perform a dependent mass spectrometry scan of the separating sample mixture for the ion at the second interval producing a spectrum for a background using the dependent scan control module.

\* \* \* \* \*